(12) United States Patent
Hildebrand et al.

(10) Patent No.: US 7,517,679 B2
(45) Date of Patent: Apr. 14, 2009

(54) **RECOMBINANT WATERMELON (*CITRULLUS LANATUS*) HYDROPEROXIDE LYASE AND USES THEREOF**

(75) Inventors: David Hildebrand, Lexington, KY (US); Hirotada Fukushige, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/540,693

(22) Filed: Oct. 2, 2006

(65) Prior Publication Data

US 2007/0083946 A1   Apr. 12, 2007

(51) Int. Cl.
  *C12N 1/21* (2006.01)
  *C12N 9/88* (2006.01)
  *C12N 1/20* (2006.01)
  *C12P 7/24* (2006.01)
  *C12N 15/70* (2006.01)
  *C07H 21/04* (2006.01)

(52) U.S. Cl. ............... 435/252.33; 435/232; 435/252.3; 435/320.1; 536/23.2

(58) Field of Classification Search ............ 435/252.33, 435/189, 69.1, 320.1, 468, 419; 536/23.2
See application file for complete search history.

(56) References Cited

U.S. PATENT DOCUMENTS

| | | | |
|---|---|---|---|
| 6,008,034 A | 12/1999 | Hausler et al. | |
| 6,238,898 B1 | 5/2001 | Hausler et al. | |
| 6,274,358 B1 | 8/2001 | Holtz et al. | |
| 6,444,874 B1 | 9/2002 | Duvick et al. | |
| 6,627,797 B1 | 9/2003 | Duvick et al. | |

OTHER PUBLICATIONS

Matsui et al. "Fatty acid 9-and 13-hydroperoxide lyases from cucumber", FEBS Letters 481, (2000) 183-188.*

"Characterization of three cloned and expressed 13-hydroperoxide lyase isoenzymes from alfalfa with unusual N-terminal sequences and different enzyme kinetics", Noordermeer, et al., Eur. J. Biochem. 267, 2473-2482 (2000).

"Fatty acid 9- and 13- hydroperoxide lyases from cucumber", Matsui, et al., 2000 Federation of European Biochemical Societies, pp. 183-188.

"Hydroperoxide lyase depletion in transgenic potato plants leads to an increase in aphid performance", Vancanneyt, et al., Apr. 30, 2001.

"Bell pepper fruit fatty acid hydroperoxide lyase is a cytochrome P450 (CYP74B)", Matsui, et al. 1996 Federation of European Biochemical Societies. pp. 21-24.

"Fatty Acid Hydroperoxide Lyase in Tomato Fruits: Cloning and Properties of a Recombinant Enzyme Expressed in *Escherichia coli*", Matsui, et al., Biosci. Biotechnol. Biochem., 64 (6), 1189-1196, 2000.

"Molecular Cloning and Expression of *Arabidopsis* Fatty Acid Hydroperoxide Lyase", Matsui, et al, Plant Cell Physiol. 40(5): 477-481 (1999).

"The purification and characterization of fatty acid hydroperoxide lyase in sunflower", Itoh, et al., Biochimica et Biophysica Acta 1436 (1999) 531-540.

"Molecular Characterization of an *Arabidopsis* Gene Encoding Hydroperoxide Lyase, a Cytochrome P-450 That is Wound Inducible", Bate, et al., Plant Physiol. (1998) 117: 1393-1400.

Guo et al., Protein tolerance to random amino acid change, Proc. Natl Acad Sci U.S.A. Jun. 22, 2004; 101(25); 9205-10, Epub Jun. 14, 2004.

* cited by examiner

*Primary Examiner*—Nashaat T Nashed
*Assistant Examiner*—Iqbal H Chowdhury
(74) *Attorney, Agent, or Firm*—McDermott Will & Emery LLP

(57) ABSTRACT

Recombinant watermelon (*Citrullus lanatus*)hydroperoxide lyase protein, DNA sequences encoding the protein, vectors containing the DNA sequences and hosts containing the vectors are provided, together with methods for recombinantly producing watermelon hydroperoxide lyase, DNA sequences, vectors and hosts.

4 Claims, 5 Drawing Sheets

*Citrullus lanatus* Hydroperoxide Lyase Peptide Sequence

```
  1  Met Lys Val Thr Met Thr Ser Gly Gly Met Pro Ser Ile Pro Ser   15
 16  Ser Ile Ser Pro Pro Pro Val Thr Leu Pro Leu Arg Asn Ile Pro   30
 31  Gly Ser Tyr Gly Leu Pro Leu Phe Gly Ser Ile Gly Asp Arg Leu   45
 46  Asp Tyr Phe Trp Phe Gln Gly Pro Glu Lys Phe Phe Arg Ser Arg   60
 61  Met Glu Lys Asn Gln Ser Thr Val Phe Arg Thr Asn Val Pro Pro   75
 76  Ser Phe Pro Phe Phe Phe Thr Asp Pro Arg Val Ile Ala Val Leu   90
 91  Asp Cys Lys Ser Phe Ala His Leu Phe Asp Met Glu Ile Val Glu  105
106  Lys Lys Asn Val Leu Val Gly Asp Phe Met Pro Ser Thr Ser Phe  120
121  Thr Gly Asn Met Arg Val Cys Ala Tyr Leu Asp Thr Ser Glu Ser  135
136  Gln His Ser Lys Ile Lys Asn Phe Val Met Asp Val Leu Arg Arg  150
151  Ser Ser Arg Ile Trp Ile Gln Glu Leu Glu Ser Asn Leu Ser Thr  165
166  Met Trp Asp Ser Ile Glu Ser Glu Ile Ala Lys Asp Thr Lys Ser  180
181  Ser Phe Arg Asn His Leu Gln Pro Thr Leu Phe Asn Phe Phe Ser  195
196  Lys Thr Leu Ala Gly Ala Asp Thr Ala Lys Ser Pro Glu Val Ala  210
211  Lys Ser Gly Tyr Ile Asp Val Ile Ile Trp Leu Gly Leu Gln Leu  225
226  Val Pro Thr Ile His Ile Gly Ile Leu Gln Pro Leu Glu Glu Ile  240
241  Phe Leu His Ser Phe Arg Leu Pro Phe Phe Pro Ile Ala Ser Arg  255
256  Tyr Gln Arg Leu Tyr Asp Phe Ile Gln Lys Glu Gly Glu Glu Val  270
271  Val Glu Arg Gly Val Ser Glu Phe Gly Leu Thr Lys Asp Glu Ala  285
286  Ile His Asn Leu Ile Phe Thr Met Gly Phe Asn Ala Tyr Gly Gly  300
301  Phe Ser Leu Phe Phe Pro Val Leu Leu Asp Arg Ile Leu Asn Asp  315
316  Lys Thr Gly Leu Gln Gln Arg Ile Leu Glu Glu Val Lys Ala Lys  330
331  Thr Gly Ser Gly Leu Thr Phe Glu Ser Val Lys Glu Met Asp Leu  345
346  Ile Tyr Ser Val Val Tyr Glu Thr Leu Arg Leu Asp Pro Pro Val  360
361  Pro Thr Gln Tyr Ala Arg Ala Arg Lys Asp Phe Lys Leu Ser Ser  375
376  Tyr Asp Ser Ala Tyr Ser Ile Lys Lys Gly Glu Leu Leu Cys Gly  390
391  Tyr Gln Pro Leu Val Met Arg Asp Pro Lys Val Phe Asn Lys Pro  405
406  Lys Thr Phe Asn Pro Gly Arg Phe Arg Gly Glu Lys Gly Ala Ala  420
421  Leu Leu Asp Tyr Leu Phe Trp Ser Asn Gly Pro Gln Thr Gly Leu  435
436  Pro Ser Glu His Asn Lys Gln Cys Ala Gly Lys Asp Leu Val Val  450
451  Leu Thr Ala Val Val Phe Val Ala Tyr Ile Phe Arg Arg Tyr Asp  465
466  Trp Ile Ala Gly Glu Gly Gly Ser Ile Thr Ala Phe Gln Arg Thr  480
481  Asn                                                           481
```

FIG. 2

*Citrullus lanatus* Hydroperoxide Lyase Nucleotide Sequence

```
   1  ATGAAGGTCACCATGACCTCCGGCGGAATGCCTTCCATACCTTCATCGATTTCGCCACCG    60
  61  CCGGTCACTTTACCGCTCAGAAATATCCCCGGCAGCTACGGTTTGCCGCTGTTCGGATCC   120
 121  ATCGGTGACCGGCTGGATTACTTCTGGTTTCAAGGACCCGAGAAGTTCTTCAGGTCTCGG   180
 181  ATGGAGAAGAATCAAAGTACGGTTTTCAGAACGAATGTTCCTCCGTCGTTCCCTTTCTTC   240
 241  TTCACCGATCCGAGAGTGATTGCGGTTCTGGATTGCAAGTCGTTTGCGCATCTATTCGAC   300
 301  ATGGAAATCGTGGAGAAGAAGAATGTTCTGGTCGGTGATTTCATGCCGAGCACAAGTTTC   360
 361  ACCGGAAATATGAGAGTCTGTGCGTATTTGGATACGTCGGAATCTCAACACTCGAAGATA   420
 421  AAAAACTTCGTCATGGACGTTCTGCGGCGGAGCTCGAGGATTTGGATACAGGAGTTGGAA   480
 481  TCGAACCTATCGACGATGTGGGACAGCATAGAATCCGAAATCGCAAAGGACACAAAATCC   540
 541  AGCTTCAGAAACCATCTCCAACCAACTCTTTTCAATTTCTTCTCCAAAACCCTGGCCGGC   600
 601  GCCGACACTGCAAAATCACCGGAAGTGGCTAAATCCGGCTACATCGACGTCATAATTTGG   660
 661  CTGGGGCTCCAGCTGGTCCCCACCATCCACATCGGCATTCTCCAACCCCTGGAAGAAATA   720
 721  TTCCTCCACTCTTTCCGATTACCCTTCTTCCCCATCGCCTCTCGCTACCAAAGACTCTAC   780
 781  GATTTCATCCAAAAAGAAGGGGAAGAAGTGGTTGAGCGAGGCGTTTCGGAGTTCGGGTTG   840
 841  AGGAAGGATGAAGCAATTCACAATCTCATCTTCACCATGGGATTCAACGCCTACGGTGGT   900
 901  TTCAGTCTCTTCTTCCCGGTTCTACTCGATCGGATACTCAACGACAAAACCGGTTTACAA   960
 961  CAGAGAATCCTCGAGGAAGTCAAGGCAAAAACCGGCTCCGGTCTGACATTCGAGTCGGTC  1020
1021  AAGGAGATGGATCTCATCTACTCCGTCGTTTACGAGACACTCCGGCTTGACCCGCCGGTT  1080
1081  CCAACCCAGTACGCGAGAGCCAGAAAGGATTTCAAGCTAAGTTCCTACGATTCAGCGTAT  1140
1141  AGCATCAAGAAAGGGGAGCTGCTTTGTGGGTATCAGCCGCTGGTGATGAGAGACCCGAAG  1200
1201  GTGTTCAATAAACCGAAGACGTTTAATCCGGGCCGGTTCCGGGGAGAGAAGGGGCGGCG  1260
1261  CTGCTGGATTATTTGTTCTGGTCGAACGGGCCGCAGACGGGACTACCGAGCGAGCATAAC  1320
1321  AAGCAGTGCGCCGGGAAGGATTTGGTGGTGCTGACGGCAGTGGTGTTCGTGGCTTACATA  1380
1381  TTTCGAAGGTATGATTGGATTGCAGGGGAAGGAGGTTCGATTACAGCTTTTCAAAGGACC  1440
1441  AACTGAAGTGAAATATATATATATATGTAGATTGAGAACTGCAGCTTTTTTTGTTCATGG  1500
1501  CTTCTTTTTTATGTATGAGTGTGGAGCCCAAATGAAAAAAATTGGAAAAATTAATCAATA  1561
1561  AAATTAAGATTCCATTTAAAAAAAAAAAAAAAAAAAAAAAGCAAAAAAAAAAAAAAAAAA  1620
1621  AAAAAAAAAAAA                                                 1632
```

FIG. 3

ClHL-N16: Watermelon HL transgenic tobacco

AtHL-N24: Arabidopsis HL transgenic tobacco

SEQUENCE LISTING

<160> NUMBER OF SEQ ID NOS: 6

<210> SEQ ID NO 1
<211> LENGTH: 481
<212> TYPE: PRT
<213> ORGANISM: Citrullus lanatus

<400> SEQUENCE: 1

```
Met Lys Val Thr Met Thr Ser Gly Gly Met Pro Ser Ile Pro Ser Ser
1               5                   10                  15

Ile Ser Pro Pro Val Thr Leu Pro Leu Arg Asn Ile Pro Gly Ser
                20                  25                  30

Tyr Gly Leu Pro Leu Phe Gly Ser Ile Gly Asp Arg Leu Asp Tyr Phe
                35                  40                  45

Trp Phe Gln Gly Pro Glu Lys Phe Phe Arg Ser Arg Met Glu Lys Asn
        50                  55                  60

Gln Ser Thr Val Phe Arg Thr Asn Val Pro Pro Ser Phe Pro Phe Phe
65                  70                  75                  80

Phe Thr Asp Pro Arg Val Ile Ala Val Leu Asp Cys Lys Ser Phe Ala
                85                  90                  95

His Leu Phe Asp Met Glu Ile Val Glu Lys Lys Asn Val Leu Val Gly
                100                 105                 110

Asp Phe Met Pro Ser Thr Ser Phe Thr Gly Asn Met Arg Val Cys Ala
                115                 120                 125

Tyr Leu Asp Thr Ser Glu Ser Gln His Ser Lys Ile Lys Asn Phe Val
                130                 135                 140

Met Asp Val Leu Arg Arg Ser Ser Arg Ile Trp Ile Gln Glu Leu Glu
145                 150                 155                 160

Ser Asn Leu Ser Thr Met Trp Asp Ser Ile Glu Ser Glu Ile Ala Lys
                165                 170                 175

Asp Thr Lys Ser Ser Phe Arg Asn His Leu Gln Pro Thr Leu Phe Asn
                180                 185                 190

Phe Phe Ser Lys Thr Leu Ala Gly Ala Asp Thr Ala Lys Ser Pro Glu
                195                 200                 205

Val Ala Lys Ser Gly Tyr Ile Asp Val Ile Ile Trp Leu Gly Leu Gln
                210                 215                 220

Leu Val Pro Thr Ile His Ile Gly Ile Leu Gln Pro Leu Glu Glu Ile
225                 230                 235                 240

Phe Leu His Ser Phe Arg Leu Pro Phe Phe Pro Ile Ala Ser Arg Tyr
                245                 250                 255

Gln Arg Leu Tyr Asp Phe Ile Gln Lys Glu Gly Glu Glu Val Val Glu
                260                 265                 270

Arg Gly Val Ser Glu Phe Gly Leu Thr Lys Asp Glu Ala Ile His Asn
                275                 280                 285

Leu Ile Phe Thr Met Gly Phe Asn Ala Tyr Gly Gly Phe Ser Leu Phe
                290                 295                 300

Phe Pro Val Leu Leu Asp Arg Ile Leu Asn Asp Lys Thr Gly Leu Gln
305                 310                 315                 320

Gln Arg Ile Leu Glu Glu Val Lys Ala Lys Thr Gly Ser Gly Leu Thr
                325                 330                 335

Phe Glu Ser Val Lys Glu Met Asp Leu Ile Tyr Ser Val Val Tyr Glu
```

```
                    340                 345                 350
Thr Leu Arg Leu Asp Pro Pro Val Pro Thr Gln Tyr Ala Arg Ala Arg
                355                 360                 365
Lys Asp Phe Lys Leu Ser Ser Tyr Asp Ser Ala Tyr Ser Ile Lys Lys
            370                 375                 380
Gly Glu Leu Leu Cys Gly Tyr Gln Pro Leu Val Met Arg Asp Pro Lys
385                 390                 395                 400
Val Phe Asn Lys Pro Lys Thr Phe Asn Pro Gly Arg Phe Arg Gly Glu
                405                 410                 415
Lys Gly Ala Ala Leu Leu Asp Tyr Leu Phe Trp Ser Asn Gly Pro Gln
            420                 425                 430
Thr Gly Leu Pro Ser Glu His Asn Lys Gln Cys Ala Gly Lys Asp Leu
        435                 440                 445
Val Val Leu Thr Ala Val Val Phe Val Ala Tyr Ile Phe Arg Arg Tyr
    450                 455                 460
Asp Trp Ile Ala Gly Glu Gly Gly Ser Ile Thr Ala Phe Gln Arg Thr
465                 470                 475                 480
Asn
```

<210> SEQ ID NO 2
<211> LENGTH: 1632
<212> TYPE: DNA
<213> ORGANISM: Citrullus lanatus

<400> SEQUENCE: 2

```
atgaaggtca ccatgacctc cggcggaatg ccttccatac cttcatcgat ttcgccaccg      60
ccggtcactt taccgctcag aaatatcccc ggcagctacg gtttgccgct gttcggatcc     120
atcggtgacc ggctggatta cttctggttt caaggacccg agaagttctt caggtctcgg     180
atggagaaga atcaaagtac ggttttcaga acgaatgttc ctccgtcgtt cccttcttc      240
ttcaccgatc cgagagtgat tgcggttctg gattgcaagt cgtttgcgca tctattcgac     300
atggaaatcg tggagaagaa gaatgttctg gtcggtgatt tcatgccgag cacaagtttc     360
accggaaata tgagagtctg tgcgtatttg gatacgtcgg aatctcaaca ctcgaagata     420
aaaaacttcg tcatggacgt tctgcggcgg agctcgagga tttggataca ggagttggaa     480
tcgaacctat cgacgatgtg ggacagcata gaatccgaaa tcgcaaagga cacaaaatcc     540
agcttcagaa accatctcca accaactctt ttcaatttct ctccaaaac  cctggccggc     600
ccgacactg caaaatcacc ggaagtggct aaatccggct acatcgacgt cataatttgg      660
ctggggctcc agctggtccc caccatccac atcggcattc tccaaccct  ggaagaaata     720
ttcctccact ctttccgatt acccttcttc cccatcgcct ctcgctacca agactctac      780
gatttcatcc aaaaagaagg ggaagaagtg gttgagcgag gcgtttcgga gttcgggttg     840
acgaaggatg aagcaattca caatctcatc ttcaccatgg gattcaacgc ctacggtggt     900
ttcagtctct tcttcccggt tctactcgat cggatactca acgacaaaac cggtttacaa     960
cagagaatcc tcgaggaagt caaggcaaaa accggctccg gtctgacatt cgagtcggtc    1020
aaggagatgg atctcatcta ctccgtcgtt tacgagacac tccggcttga cccgccggtt    1080
ccaacccagt acgcgagagc cagaaaggat ttcaagctaa gttcctacga ttcagcgtat    1140
agcatcaaga aggggagct gctttgtggg tatcagccgc tggtgatgag agacccgaag    1200
gtgttcaata aaccgaagac gtttaatccg ggccggttcc ggggagagaa ggggcggcg     1260
ctgctggatt atttgttctg gtcgaacggg ccgcagacgg gactaccgag cgagcataac    1320
```

```
aagcagtgcg ccgggaagga tttggtggtg ctgacggcag tggtgttcgt ggcttacata    1380
tttcgaaggt atgattggat tgcagggaa ggaggttcga ttacagcttt tcaaaggacc    1440
aactgaagtg aaatatatat atatatgtag attgagaact gcagctttt ttgttcatgg    1500 cttctttttt atgtatgagt gtggagccca aatgaaaaaa attggaaaaa ttaatcaata    1560
aaattaagat tccatttaaa aaaaaaaaaa aaaaaaaaaa gcaaaaaaaa aaaaaaaaaa    1620
aaaaaaaaaa aa                                                        1632

<210> SEQ ID NO 3
<211> LENGTH: 27
<212> TYPE: DNA
<213> ORGANISM: Artificial Sequence
<220> FEATURE:
<223> OTHER INFORMATION: Artificial sequence derived from partial
      watermelon Hydroperoxide lyase sequence

<400> SEQUENCE: 3
ccggctccgg tctgacattc gagtcgg                                          27

<210> SEQ ID NO 4
<211> LENGTH: 29
<212> TYPE: DNA
<213> ORGANISM: Artificial Sequence
<220> FEATURE:
<223> OTHER INFORMATION: Artificial sequence derived from partial
      watermelon hydroperoxide lyase sequence

<400> SEQUENCE: 4
gctcgctcgg tagtcccgtc tgcggcccg                                        29

<210> SEQ ID NO 5
<211> LENGTH: 29
<212> TYPE: DNA
<213> ORGANISM: Artificial Sequence
<220> FEATURE:
<223> OTHER INFORMATION: Artificial sequence designed from watermelon
      hydroperoxide lyase gene

<400> SEQUENCE: 5
cgcactagta tgaaggtcac catgacctc                                        29

<210> SEQ ID NO 6
<211> LENGTH: 29
<212> TYPE: DNA
<213> ORGANISM: Artificial Sequence
<220> FEATURE:
<223> OTHER INFORMATION: Artificial sequence designed from watermelon
      hydroperoxide lyase gene

<400> SEQUENCE: 6
ggtaagcttc agttggtcct ttgaaaagc                                        29
```

US 7,517,679 B2

RECOMBINANT WATERMELON (CITRULLUS LANATUS) HYDROPEROXIDE LYASE AND USES THEREOF

RELATED APPLICATION

This application claims priority to U.S. application Ser. No. 10/718,265, filed Nov. 21, 2003, which is hereby incorporated in its entirety.

FIELD OF THE INVENTION

This invention relates to the production of a hydroperoxide lyase (HL) protein in host cells via recombinant expression of the protein. Recombinant HL protein, DNA sequences encoding the protein, vectors containing these DNA sequences and hosts containing the vectors are provided, together with methods for recombinantly producing such protein, DNA sequences, vectors and hosts.

BACKGROUND OF THE INVENTION

Fatty acid hydroperoxide lyase (HL) is an enzyme of the octadecanoid pathway that cleaves a C—C bond in the hydroperoxides of polyunsaturated fatty acids to generate aldehydes and ω-oxo-acids. This enzyme is widely distributed in plants and is involved in the biosynthesis of volatile aldehydes and alcohols. Its presence in plants can be recognized by the fact that crushed leaves of nearly every plant generate a grassy smell that is characteristic of $C_6$-aldehydes. The short-chain volatile aldehydes and their reduced derivatives, alcohols, are important constituents of the characteristic flavors of fruits, vegetables and green leaves.

The six-carbon volatile compounds, leaf aldehyde [(2E)-hexanal] and leaf alcohol [(3Z)-hexanol], are important components of the aroma and flavor of fruits and vegetables and are associated with 'green notes' of leaves. These compounds are widely used as flavors in foods and beverages and some of the $C_6$-aldehydes are also reported to have anti-microbial properties. These volatile compounds are produced by fatty acid hydroperoxide lyase (HL) by cleaving 13-hydroperoxy fatty acids, mainly from linolenic and linoleic acids.

Commercial production of natural 'green note' compounds is generally achieved by fractional distillation of essential oils such as mint oil or by the combined action of lipoxygenase and hydroperoxide lyase on unsaturated fatty acids using plant material from different sources. These processes provide low yields and are dependant on specific plant materials. Therefore, there is a need for improved methods of generating 'green note' compounds.

SUMMARY OF THE INVENTION

It has now been found that high reproducible yields of "green note" compounds (e.g., [(2E)-hexanal] can be obtained independent of plant materials and in the absence of unwanted side reaction (e.g. isomerase activity) by transfer of the gene coding for HL from plant into host cells, subsequent expression of the gene, addition of linolenic acid as substrate and lipoxygenase (or soybean as the enzyme source) to produce the leaf aldehyde [(2E)-hexanal].

Thus, in a first aspect of this invention, there are provided isolated DNA sequences encoding a protein having the amino acid sequence of SEQ ID NO: 1. In a preferred embodiment the isolated nucleic acid encodes a polypeptide having at least about 90% amino acid sequence similarity to SEQ ID NO: 1 and having HL activity.

In another aspect of the invention, there is provided an expression vector comprising a nucleic acid molecule encoding a polypeptide having at least about 90% sequence similarity to SEQ ID NO: 1 and having HL activity.

In yet another aspect of the invention there is provided a host cell transformed with an expression vector comprising a nucleic acid molecule encoding a polypeptide having at least about 90% sequence similarity to SEQ ID NO: 1 and having HL activity. In a preferred embodiment the host cell is E. coli.

In another aspect of the invention there is provided a method of making hydroperoxide lyase comprising culturing a host cell transformed with an expression vector comprising a nucleic acid molecule encoding a polypeptide having at least about 90% sequence similarity to SEQ ID NO: 1 and having HL activity under conditions that enable expression of the nucleic acid, and isolating the polypeptide from the host cells.

The invention also provides transgenic plants comprising a recombinant nucleic acid molecule comprising a nucleic acid molecule encoding a polypeptide having at least about 90% sequence similarity to SEQ ID NO: 1 and having HL activity.

In another aspect of the invention there is provided a method for producing green note compounds comprising reacting fatty acid hydroperoxide in the presence of isolated recombinant protein having the amino acid sequence of SEQ ID NO: 1 or a polypeptide having at least about 90% sequence similarity to SEQ ID NO: 1 and having HL activity; and reacting the resulting aliphatic aldehydes in the presence of isomerase and/or alcohol dehydrogenase.

BRIEF DESCRIPTION OF THE DRAWINGS

FIG. 2 is the amino acid sequence of the watermelon (Citrullus lanatus) hydroperoxide lyase (SEQ ID NO: 1).

FIG. 3 is the nucleotide sequence of the watermelon (Citrullus lanatus) hydroperoxide lyase gene (SEQ ID NO: 2).

DETAILED DESCRIPTION OF THE INVENTION

Figure 1:
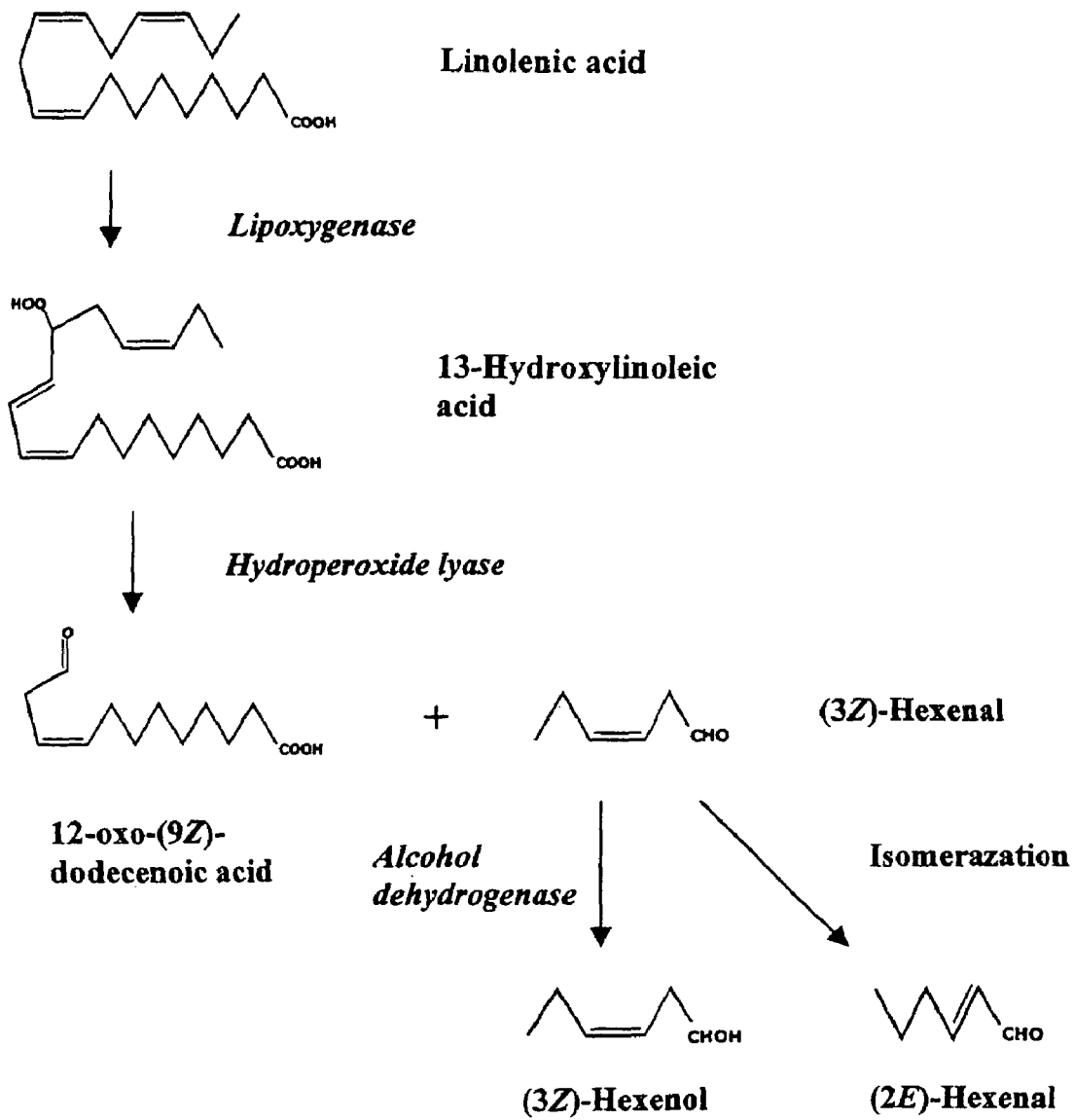
FIG. 1 is a schematic drawing of the hydroperoxide lyase pathway.

Fatty acid hydroperoxide lyase (HL) has been cloned from a variety of sources. The gene was first cloned from the bell pepper fruit. (Matsui et al., 1996). Moxon et al. reported in 1997 that the product of the cDNA associated with an Arabidopsis EST sequence 94J16 has HL activity when expressed in E. coli. Both Bate et al. (1998) and Matsui et al., (1999) have since confirmed that this Arabidopsis cDNA encodes an HL. Many additional HLs have been identified and cloned from several plant species, including tomatoes and potatoes. However, until now, the gene has not been isolated from watermelon, whose leaves are reported to be among the highest $C_6$-aldehyde producers among plant tissues.

A watermelon (Citrullus lanatus) HL cDNA was cloned via RT-PCR. For cloning the gene, degenerate primers were designed based on conserved sequences of published sequences of several HL and AOS genes. The full sequence of the HL cDNA obtained using the primers was determined using RACE. The nucleotide sequence of the *Citrulus lanatus* HL gene is shown in FIG. 3, while the derived amino acid sequence is shown in FIG. 2. The watermelon polypeptide sequence has highest sequence similarity to cucumber 13-HL and 63, 59, 59, 58, 57 and 47% sequence identity with HL from guava, tomato, *Nicotania attenuate*, potato, alfalfa, green pepper, *Arabidopsis* and barley, respectively.

As used herein the term "substantially homologous," means that a particular sequence, for example, a mutant sequence, varies from a reference sequence by one or more substitutions, deletions, or additions, the net effect of which does not result in an adverse functional dissimilarity between the reference and subject sequences. For purposes of the present invention, DNA sequences having at least 90 percent homology (or sequence similarity), encoding equivalent biological properties, and showing equivalent expression characteristics are considered substantially homologous. Sequences having lesser degrees of homology, encoding comparable HL activity, and showing equivalent expression characteristics, e.g., fragments of the nucleotide sequence SEQ ID NO: 2 are considered substantial equivalents. Generally, homologous DNA sequences can be identified by cross-hybridization under standard hybridization conditions of moderate stringency.

The present invention also provides vectors and expression vectors containing the DNA sequences of the present invention, hosts containing such vectors for the production of proteins with HL activity, and processes for the production of such DNA sequences, recombinant vectors and host cells.

The invention also provides recombinant proteins with HL activity. Specifically a protein with HL activity is defined to include a polypeptide having the amino acid sequence SEQ ID NO: 2 or any protein or polypeptide having an amino acid sequence which is substantially homologous to the amino acid sequence SEQ ID NO: 2 and further having the following biological activity: When the protein or polypeptide is incubated under suitable conditions and a suitable amount of substrate such as 13-(S)-linolenic acid hydroperoxide is added, the formation of (3Z)-hexenal and (2E)-hexenal is observed.

As used herein the term recombinant proteins having at least about 90% sequence similarity to SEQ ID NO: 1 and having HL activity includes proteins modified deliberately, as for example, by addition of specific sequences that preferably bind to an affinity carrier material. Examples of such sequences are sequences containing at least two adjacent histidine residues (see in this respect European Patent No. 282 042). Such sequences bind selectively to nitrilotriacetic acid nickel chelate resins (Hochuli and Dobeli, Biol. Chem. Hoope-Seyler 368, 748 (1987); European Patent No. 253 303). Proteins with HL activity which contain such a specific sequence can, therefore, be separated selectively from the remaining polypeptides. The specific sequence can be linked either to the C-terminus or the N-terminus of the proteins with HL activity.

Methods for the expression, isolation and purification of watermelon HL proteins and proteins having at least about 90% sequence similarity to SEQ ID NO: 1 and having HL activity are also provided. For example, recombinant HL protein can be prepared by cloning of DNA sequences encoding proteins with HL activity. DNA sequences encoding proteins with HL activity can be cloned using a variety of techniques. Using the methods described in this application cDNAs encoding proteins with HL activity or fragments thereof can be produced. These cDNAs can be isolated and amplified by PCR technique using oligodeoxynucleotide DNA primers by conventional techniques.

The cDNA (SEQ ID NO: 2) encoding the amino acid sequence SEQ ID NO: 1 was obtained using the DNA primers described in the examples. By using conventional techniques, this cDNA has been isolated from RT-PCR products using RNA derived from watermelon (*Citrulus lanatus*) leaves. A RT-PCR band of an expected size was obtained from watermelon leaf total RNA using a degenerate primer pair. The full length watermelon HL cDNA was isolated and cloned into a CMV 35S-driven binary vector.

The cDNA may be obtained not only from RT-products, but by other conventional techniques, e.g., by cloning genomic DNA, or fragments thereof, purified from the desired cells or plant tissues. These procedures are described by Sambrook et al., in "DNA Cloning: A Practical Approach", Vol. I and II, D. N. Glover, ed., 1985, MRL Press, Ltd., Oxford, U. K; Benton and Davis, Science 196, 180-182 (1977); and Grunstein and Hogness, Proc. Nat. Acad. Sci. 72, 3961-3965 (1975).

To obtain cDNA encoding watermelon proteins with HL activity cDNA libraries obtained using RNA isolated from watermelon leaf may be screened by conventional DNA hybridization techniques by the methods of Benton and Davis, supra, or Grunstein and Hogness, supra, using labeled HL gene fragments, for example. Clones which hybridize to the labeled gene fragments are analyzed, e.g., by restriction endonuclease cleavage or agarose gel electrophoresis. After isolating several positive clones the positive insert of one clone is subcloned, e.g., into phagemids, and sequenced by conventional techniques.

Clones derived from genomic DNA may contain regulatory and intron DNA regions in addition to coding regions; clones derived from cDNA will not contain intron sequences. In the molecular cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Whatever the source, the DNA sequence encoding proteins with HL activity may be cloned into a suitable vector for propagation of the DNA by methods known in the art. Any commercially available vector may be used. For example, the DNA may be inserted into a CMV-S35 promoter-driven binary vector. Appropriate vectors for use with bacterial hosts are described by Pouwels et al., in "Cloning Vectors: A Laboratory Manual", 1985, Elsevier, N.Y. As a representative but nonlimiting example, useful cloning vectors for bacterial use can comprise a selectable marker and a bacterial origin of replication derived from commercially available plasmids which are in turn derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA).

The DNA sequences encoding proteins with HL activity inserted in these commercially available vectors can be verified by methods known in the art, e.g., by standard nucleotide sequencing techniques.

DNA sequences that code for proteins with HL activity from plants other than watermelon may be used herein. Accordingly, while specific DNA has been cloned and sequenced in relation to the DNA sequence in watermelon leaves, any plant cell or tissue potentially can be used as the nucleic acid source of the protein with HL activity. DNA sequences having at least about 90% sequence similarity to SEQ ID NO: 2 are then selected for use in the present invention.

Cloned DNA sequences that code for watermelon proteins having HL activity or DNA sequences that encode a polypeptide having at least about 90% sequence similarity to SEQ ID NO: 1 and having HL activity can be expressed in hosts to enable the production of these proteins with greater efficiency. Techniques for these genetic manipulations are specific for the different available hosts and are known in the art.

For expression of proteins with HL activity in hosts, in principle, all vectors which replicate and express DNA sequences encoding the proteins with HL activity in the chosen host are suitable. Expression vectors suitable for use in prokaryotic host cells are mentioned, for example, in the textbook "Molecular Cloning—A Laboratory Manual", Cold Spring Harbor Laboratory (1982), of Maniatis et al. Examples of other vectors are plasmids of the pDS family (Bujard et al., Methods in Enzymology, eds. Wu and Grossmann, Academic Press, Inc., Vol. 155, 416-433 (1987)).

Such prokaryotic expression vectors which contain the DNA sequences coding for proteins with HL activity operatively linked with an expression control sequence can be incorporated using conventional methods into any suitable prokaryotic host cell. The selection of a suitable prokaryotic host cell is determined by different factors which are well-known in the art.

Suitable prokaryotic host organisms include gram-negative and gram-positive bacteria, for example E. coli and B. subtilis strains. Examples of prokaryotic host organisms are E. coli strain M15 (described as strain OZ 291 by Villarejo et al. in J. Bacteriol. 120, 466-474 [1974] and E. coli W3110 [ATCC No. 27325]). In addition to the aforementioned E. coli strains, however, other generally accessible E. coli strains such as E. coli 294 (ATCC No. 31446) and E. coli RR1 (ATCC No. 31343) can also be used.

Plants can also be used as hosts for the recombinant production of proteins with HL activity. Transfer of the gene coding for the protein with HL activity may be achieved by a variety of methods (for review see Potrykus and Spangenberg, eds., Gene transfer to plants. A laboratory manual, Springer Verlag, Heidelberg, Germany (1995)), whereby the HL gene is integrated into the chromosome of the host plant. Homologous expression—overexpression—of the protein with HL activity can be achieved, for example, by transforming a watermelon plant with the nucleic acid of SEQ ID NO: 2 or a nucleic acid encoding a polypeptide having at least about 90% sequence similarity to SEQ ID NO: 1 and having HL activity. Other examples for plant hosts for the production of recombinant HL protein include, but are not limited to maize (*Zea mays*, Ishida et al., Nature Biotechnology 14, 745-750 (1996)), flax (*Linum usitatissimum*, Dong and Mchughen, Plant Sci. 88 (1), 61-71 (1993)) and soybean (*Glycine max*, Christou et al., Tibtech 8, 145-151 (1990)).

Transgenic plants of the invention can be used as a source or green note compounds, for example, by homogenizing plant tissues or biomass with linolenic acid and lipoxygenase or soybean as an enzyme source. Also, the nucleic acids of the invention can be expressed in microorganisms, such as bacteria and yeast, and their biomass can be used in the same way to produce green note compounds. The green note compounds can be isolated from the transformed organisms by any process known to those of skill in the art.

For the isolation of small amounts of proteins with HL activity expressed in prokaryotic host cells for analytical purposes, e.g., for polyacrylamide gel electrophoresis, the host cells can be disrupted by treatment with a detergent, e.g., sodium dodecyl sulphate (SDS). Larger quantities of the HPO lyase protein can be obtained by mechanical [Charm et al., Meth. Enzymol. 22, 476-556 (1971)], enzymatic (lysozyme treatment) or chemical (detergent treatment, urea or guanidinium hydrochloride treatment, etc.) treatments followed by use of known methods, e.g., by centrifugation at different gravities, precipitation with ammonium sulphate, dialysis (at normal pressure or at reduced pressure), preparative isoelectric focusing, preparative gel electrophoresis or by various chromatographic methods such as gel filtration, high performance liquid chromatography (HPLC), ion exchange chromatography, reverse phase chromatography and affinity chromatography (e.g., on Sepharose.RTM. Blue CL-6B).

The proteins of the invention that have HL activity can be used in the production of natural "green note" compounds by catalyzing the formation of aldehydes from fatty acid hydroperoxide. The term "green note" compounds relates to leaf aliphatic aldehydes and leaf aliphatic alcohols, e.g., (3Z)-hexenol and (2E)-hexenal. Hence the present invention also provides a process for the production of natural "green note" compounds, which process comprises the steps of:

a) reacting fatty acid hydroperoxide in the presence of a protein having the amino acid sequence of SEQ ID NO: 1 or a polypeptide having at least about 90% sequence identity to SEQ ID NO: 1 and having HL activity; and b) reacting the resulting aliphatic aldehydes in the presence of isomerase and/or alcohol dehydrogenase.

In the process for the production of "green note" compounds the watermelon HL protein can be used in isolated form, or alternatively, in form of cell-free extracts obtained from host cells containing vectors for the production of protein with HL activity. In a preferred embodiment of the invention, the process for the production of natural "green note" compounds is employed to produce (3Z)-hexenol. A preferred process for producing (3Z)-hexenol comprises the steps of:

a) reacting 13-(S)-hydroperoxide linolenic acid and/or hydrolyzed linseed oil in the presence of recombinant proteins of the invention having HL activity; and b) reducing the resulting (3Z)-hexanal with alcohol dehydrogenase.

The green note compounds, e.g. (2E)-hexenal and (3Z)-hexenol, prepared by the process of the present invention can be used as odorant and/or flavorant and worked into odorant and/or flavorant compositions in a manner known in the art.

Having now generally described this invention, the same will become better understood by reference to the specific examples, which are included herein for purpose of illustration only and are not intended to be limiting unless otherwise specified.

EXAMPLE 1

Cloning of Full Length cDNA of Watermelon Hydroperoxide Lyase

A pair of degenerate primers was designed from published HL sequences of several plants and synthesized. Total RNA was isolated from watermelon leaf tissues using the Trizol® reagent (Life Technologies) and the protocol suggested by the manufacturer. RT-PCR was conducted using the total RNA as template and a RT-PCR band of ~500 base pairs, which is the expected size for a HL protein was obtained. The RT-PCR product was partially sequenced, demonstrating that the RT-PCR product contained a portion of the coding region of watermelon HL.

Sequencing of the full length cDNA was accomplished using Clontech's SMART RACE kit. Two primers were designed from the partial sequence obtained:

```
Forward primer:
CCG GCT CCG GTC TGA CAT TCG AGT CGG  (SEQ ID NO: 3)

Reverse primer:
GCT CGC TCG GTA GTC CCG TCT GCG GCC  (SEQ ID NO: 4)
CG
```

With these gene-specific primers and primers supplied by the kit, the sequence of the coding region of the watermelon HL was obtained.

From the sequence obtained, the following primer pair was designed for cloning the full length cDNA of watermelon HL:

```
5'-end primer:
CGC ACT AGT ATG AAG GTC ACC ATG ACC  (SEQ ID NO: 5)
TC

3'-end primer:
GGT AAG CTT CAG TTG GTC CTT TGA AAA  (SEQ ID NO: 6)
GC
```

The 5'-end primer was designed to contain the SpeI-recognition site just before the start codon, while the 3'-end primer contained the HindIII recognition site just after the stop codon. The PCR product obtained using this primer pair was ligated into cloning vector pGEM-T Easy (Promega) by TA ligation.

EXAMPLE 2

Expression of Watermelon Hydroperoxide Lyase cDNA in Plants

The isolated cDNA was then digested with SpeI and ligated into a CMV 35S promoter-driven binary vector pKYLX71:35S2 digested with XbaI, which produces a compatible 5'-extension. The binary vector was transferred into *Agrobacterium tumefaciens* strain GV3850 using freeze-thaw method and its integrity was confirmed by PCR. Using *Agrobacterium* containing the watermelon HL, tobacco plants were transformed by a leaf disc method, and the transgenic lines were selected for antibiotic resistance. The HL activity of the tobacco leaf tissues was analyzed and confirmed that transformation and expression of the watermelon HL cDNA had occurred. The enzyme extracts obtained from leaf tissues were reacted with 13-hydroperoxy linolenic acid in the presence of yeast alcohol dehydrogenase (ADH) and NADH, where the production of aldehydes was measured by the reduction of NAD consumed by ADH converting aldehyde to alcohol spectrophotometrically. The products formed from 13-hydroperoxy linolenic acid in the leaf tissues of the transformed tobacco leaf were confirmed to be (3Z)-hexenal and (2E)-hexenal by GC-MS.

EXAMPLE 3

Comparison of Hydroperoxide Lyase Activity in Transgenic Plants

Figure 4:
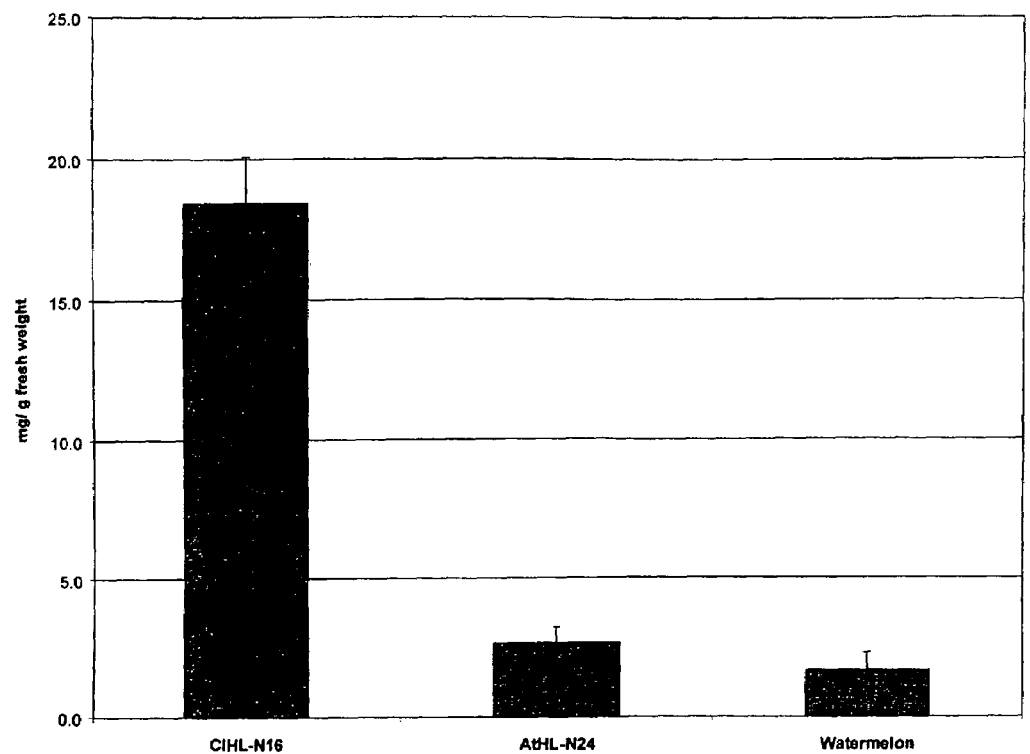
FIG. 4 is a bar graph showing the activity of HL overexpressed in tobacco plants. N lines contain watermelon HL; WT is a non-transformed tobacco plant line; and A24 is the highest expresser of Arabidopsis HL.

To compare the watermelon HL activity with another HL gene, HL cDNA was isolated from *Arabidopsis* and transgenic tobacco plants were generated following the same procedure described in example 2. HL activity was measured spectrophtometrically as described in example 2. The results shown in FIG. 4 demonstrated the much higher activity of watermelon HL than *Arabidopsis* HL.

EXAMPLE 4

Comparison of $C_6$ Aldehyde Production from Transgenic Plants

Figure 5:
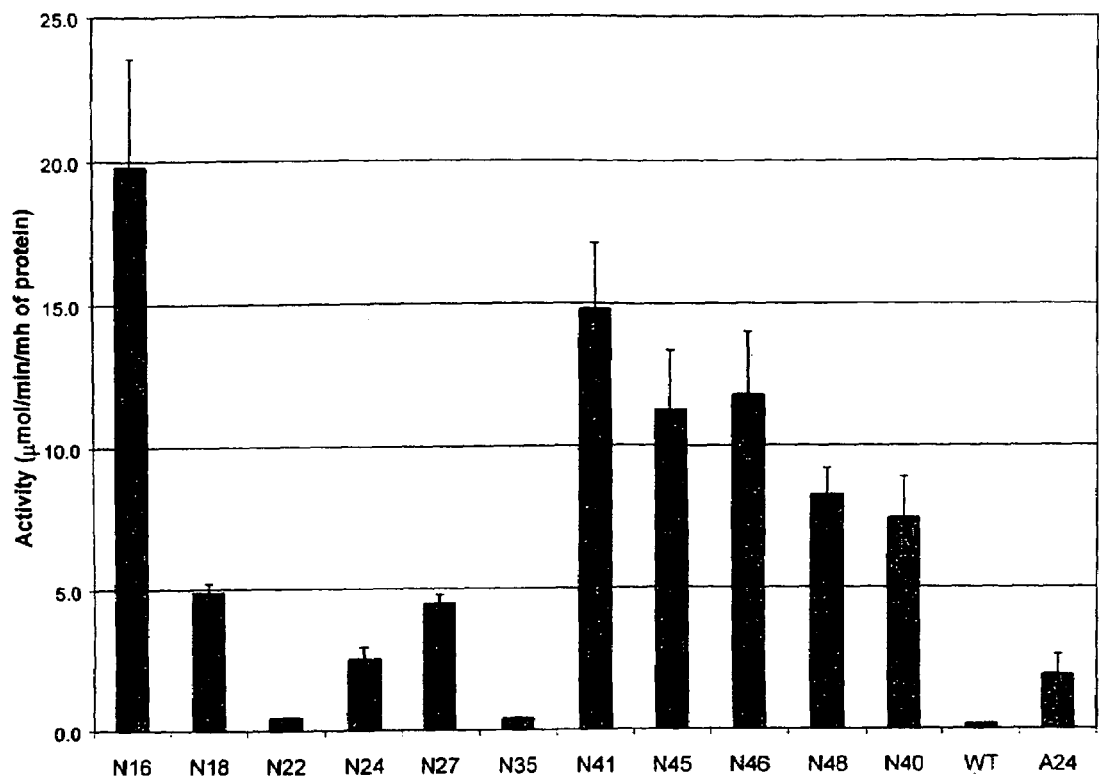
FIG. 5 is a bar graph showing $C_6$-aldehyde formation from HL over-expressed in tobacco leaves in comparison to normal (non-transformed) watermelon leaves. ClHL-Ni6: watermelon HL transgenic tobacco; AtHL-N24: Arabidopsis HL transgenic tobacco.

Twenty mg of leaf tissues of transgenic tobacco plants over-expressing watermelon HL or *Arabidopsis* HL or watermelon were homogenized with 5 mg of linolenic acid (Sigma) and 25 mg of soybean acetone powder as a lipoxygenase source in 2.0 mL of water at room temperature for 3 minutes. 0.224 mg (2.0 micromole) of (2E)-heptenal was added as an internal standard. The reaction products were extracted with 1 mL of pentane and analyzed with GC-MS. The results shown in FIG. 5 demonstrated the higher production rate of (3Z)-hexenal by watermelon HL expressed in tobacco plants than *Arabidopsis* HL as well as watermelon leaves.

EXAMPLE 5

Comparison of Hydroperoxide Lyases *C. lanatus*, *Arabidopsis thaliana* and *N. tabacum* Expressed in *E. coli*

To compare the relative activities HLs from *C. lanatus* (ClHL), *Arabidopsis* (AtHL) and *N. tabacum* (NtHL), we produced these proteins in *E. coli* and measured HL enzyme activity in crude extracts of the *E. coli* cultures. Table I demonstrates that these clones all possesses HL enzyme activity when compared to the vector control. Activity for the full-length ClHL protein was considerably higher (approximately 250-fold or more) compared to NtHL and AtHL.

TABLE I

HL activity of crude *E. coli* extracts containing $(His)_6$-tagged protein or $(His)_6$-tagged fusion protein

| *E. coli* lysates expressing the following constructs | HL Activity (nmol/mg protein/min) |
| --- | --- |
| vector control | 9.02 ± 2 |
| ClHL-3-3 lysate | 2,379 ± 516 |
| NtHL-F6-3 lysate | 28 ± 2.4 |
| AtHL-F5-14 lysate | 57 |

Values represent means±SE of replicates (n=3-6) except the AtHL for which we only have one replicate so far.

---

What is claimed is:

1. An isolated nucleic acid sequence comprising a nucleotide sequence selected from the group consisting of
   (a) the nucleotide sequence of SEQ ID NO:2;
   (b) the nucleotide sequence which is the complement of (a);
   (c) a nucleotide having at least 90% sequence similarity to SEQ ID NO:2, wherein said nucleotide sequence encodes a polypeptide having hydroperoxide lyase (HL) activity.

2. A vector comprising a nucleic acid sequence comprising a nucleotide sequence selected from the group consisting of:
   (a) the nucleotide sequence of SEQ ID NO:2,
   (b) the nucleotide sequence which is the complement of (a); and
   (c) a nucleotide sequence having at least 90% sequence similarity to SEQ ID NO:2, wherein said nucleotide sequence encodes a polypeptide having hydroperoxide lyase (HL) activity.

3. A prokaryotic host cell transformed with a vector comprising a nucleic acid sequence selected from the group consisting of:
(a) the nucleotide sequence of SEQ ID NO:2,
(b) the nucleotide sequence which is the complement of (a); and
(c) a nucleotide sequence having at least 90% sequence similarity to SEQ ID NO:2, wherein said nucleic acid sequence encodes a polypeptide having HL activity.

4. The host cell of claim 3 wherein the host cell is *E. coli*.

* * * * *